United States Patent
Furukawa

(10) Patent No.: US 10,493,245 B2
(45) Date of Patent: Dec. 3, 2019

(54) GUIDE WIRE

(71) Applicant: ASAHI INTECC CO., LTD., Seto-shi, Aichi (JP)

(72) Inventor: Muneya Furukawa, Seto (JP)

(73) Assignee: ASAHI INTECC CO., LTD., Seto-shi (JP)

( * ) Notice: Subject to any disclaimer, the term of this patent is extended or adjusted under 35 U.S.C. 154(b) by 85 days.

(21) Appl. No.: 15/441,634

(22) Filed: Feb. 24, 2017

(65) Prior Publication Data

US 2017/0259040 A1   Sep. 14, 2017

Related U.S. Application Data

(63) Continuation of application No. PCT/JP2016/057539, filed on Mar. 10, 2016.

(51) Int. Cl.
*A61M 25/09* (2006.01)
*A61B 17/12* (2006.01)

(52) U.S. Cl.
CPC ..... *A61M 25/09* (2013.01); *A61M 2025/09083* (2013.01); *A61M 2025/09175* (2013.01); *A61M 2025/09191* (2013.01)

(58) Field of Classification Search
CPC ........ A61M 25/09; A61M 2025/09083; A61M 2025/09175; A61M 2025/09191; A61B 17/12022
See application file for complete search history.

(56) References Cited

U.S. PATENT DOCUMENTS

| | | | | |
|---|---|---|---|---|
| 4,456,017 A * | 6/1984 | Miles | ............ | A61M 25/09033 600/585 |
| 6,251,086 B1 * | 6/2001 | Cornelius | ............ | A61L 31/10 600/585 |
| 6,638,267 B1 * | 10/2003 | Esselstein | ............ | A61M 25/09 604/247 |
| 7,025,734 B1 * | 4/2006 | Ellis | ............ | A61B 5/14542 600/345 |

(Continued)

FOREIGN PATENT DOCUMENTS

EP  2 810 683 A1  12/2014
EP  2918306 A1    9/2015
(Continued)

OTHER PUBLICATIONS

Apr. 3, 2018 Extended European Search Report issued in European Application No. 16829222.5.
(Continued)

*Primary Examiner* — Sean P Dougherty
(74) *Attorney, Agent, or Firm* — Oliff PLC

(57) ABSTRACT

A guide wire includes a core shaft, a coil body disposed around an outer periphery of the core shaft, and a joining portion joining a distal end of the core shaft to a distal end of the coil body 3. An outer periphery of the joining portion has, at its proximal end, an uneven shape in a longitudinal direction of the guide wire. The outer periphery may include a protruded portion that protrudes proximally in the longitudinal direction, and a recessed portion that protrudes distally in the longitudinal direction. The guide wire has improved joining strength between the joining portion and the coil body, preventing the joining portion from detaching from the coil body.

11 Claims, 9 Drawing Sheets

(56) References Cited

U.S. PATENT DOCUMENTS

| | | | | |
|---|---|---|---|---|
| 7,169,118 B2* | 1/2007 | Reynolds | A61M 25/09 | 600/585 |
| 7,532,920 B1* | 5/2009 | Ainsworth | A61B 5/02007 | 600/341 |
| 7,955,272 B2* | 6/2011 | Rooney | A61M 25/09 | 600/585 |
| 8,702,626 B1* | 4/2014 | Kim | A61M 25/09041 | 600/585 |
| 8,968,216 B2* | 3/2015 | Terashi | A61B 17/3207 | 600/585 |
| 2002/0151823 A1* | 10/2002 | Miyata | A61B 5/6851 | 600/585 |
| 2003/0083622 A1* | 5/2003 | Osawa | A61M 25/09 | 604/164.13 |
| 2007/0185415 A1 | 8/2007 | Ressemann et al. | | |
| 2007/0198044 A1* | 8/2007 | Lupton | A61M 25/09 | 606/191 |
| 2008/0281230 A1* | 11/2008 | Kinoshita | A61M 25/09 | 600/585 |
| 2011/0152721 A1* | 6/2011 | Sela | A61B 5/06 | 600/585 |
| 2011/0208092 A1* | 8/2011 | Nishigishi | A61M 25/09 | 600/585 |
| 2012/0029476 A1* | 2/2012 | Kanazawa | A61M 25/09 | 604/528 |
| 2012/0041420 A1* | 2/2012 | Nagano | A61M 25/09 | 604/528 |
| 2013/0267934 A1* | 10/2013 | Eskuri | A61M 25/09 | 604/528 |
| 2013/0304035 A1* | 11/2013 | Cabiri | A61B 17/00234 | 604/528 |
| 2014/0350568 A1* | 11/2014 | Shekalim | A61M 25/09 | 606/127 |
| 2015/0238734 A1 | 8/2015 | Kanazawa | | |
| 2016/0324616 A1* | 11/2016 | Zenz-Olson | A61B 17/56 | |
| 2016/0331405 A1* | 11/2016 | Keady | A61B 8/12 | |
| 2016/0331943 A1* | 11/2016 | Lupton | A61M 25/09 | |

FOREIGN PATENT DOCUMENTS

| | | |
|---|---|---|
| JP | 2014-161705 A | 9/2014 |
| JP | 2015-171519 A | 10/2015 |

OTHER PUBLICATIONS

Jun. 11, 2019 Office Action issued in Korean Patent Application No. 10-2017-7001925.

* cited by examiner

GUIDE WIRE

CROSS REFERENCE TO RELATED APPLICATION

This application is a continuation of PCT/JP2016/057539 filed on Mar. 10, 2016, the contents of which are incorporated by reference herein in their entirety.

BACKGROUND

The disclosed embodiments relate to a medical device. Specifically, the disclosed embodiments relate to a guide wire used as a guide for inserting a catheter into a lumen in the body such as a blood vessel or a ureter, and for inserting an indwelling device into a site of an aneurysm formed in a blood vessel.

A guide wire used as a guide for inserting a catheter into a lumen in the body and for inserting an indwelling device into a site of an aneurysm formed in a blood vessel generally comprises a core shaft, a coil body covering a distal end part of the core shaft, a distal end joining portion joining a distal end of the core shaft to a distal end of the coil body, and a proximal end joining portion joining the core shaft to a proximal end of the coil body.

For example, US 2007/0185415 describes a guide wire comprising a core wire (hereafter referred to as a core shaft), a coil body covering a distal end part of the core shaft, and a proximal end joining portion joining a distal end of the core shaft to a proximal end of the coil body. A distal end joining portion is joined to a distal end of the coil body (see, for example, FIG. 12A and FIG. 12B of US 2007/0185415).

In order to insert a catheter into a patient's body, for example, an operator inserts the guide wire described in US 2007/0185415 into the patient's body so that it advances toward a narrowed segment or the like in the patient's body, and then penetrates the narrowed segment. However, the guide wire may become stuck at the narrowed segment when the operator tries to penetrate the narrowed segment with the guide wire. If that happens, the operator will try to push, pull, or rotate a connector fixed at a proximal end part of the guide wire to release the guide wire from the narrowed segment.

However, in the case of a conventional guide wire, the distal end joining portion of the guide wire may detach from the coil body when the operator tries to push, pull, or rotate the stuck guide wire. If the distal end joining portion detaches from the coil body, the detached distal end joining portion may be left in the patient's body, complicating any subsequent treatment.

SUMMARY

The disclosed embodiments have been devised in order to address the above problem. An object of the disclosed embodiments is to provide a guide wire in which the joining strength between a distal end joining portion of the guide wire and a coil body is improved, preventing the distal end joining portion from detaching from the coil body.

In order to achieve the above object, a guide wire of the disclosed embodiments comprises a core shaft, a coil body covering an outer periphery of the core shaft, and a joining portion joining a distal end of the core shaft to a distal end of the coil body. An outer periphery of the joining portion has at its proximal end an uneven shape in the longitudinal direction of the guide wire. Therefore, the joining strength between the joining portion and the coil body is improved, preventing the joining portion from detaching from the coil body.

The guide wire may include a protruded portion that protrudes proximally in the longitudinal direction and a recessed portion beyond which the protruded portion extends proximally. The recessed portion may be formed in a curved fashion, which prevents stress from concentrating at the joining portion when the guide wire is bent. This in turn prevents the joining portion from detaching from the coil body.

The coil body may be formed by spirally winding two or more twisted wires, each twisted wire having multiple element wires twisted together. The guide wire can therefore be formed in a simpler manner.

DETAILED DESCRIPTION OF EMBODIMENTS

Below, the embodiments will be described with reference to the drawings.

Figure 1:
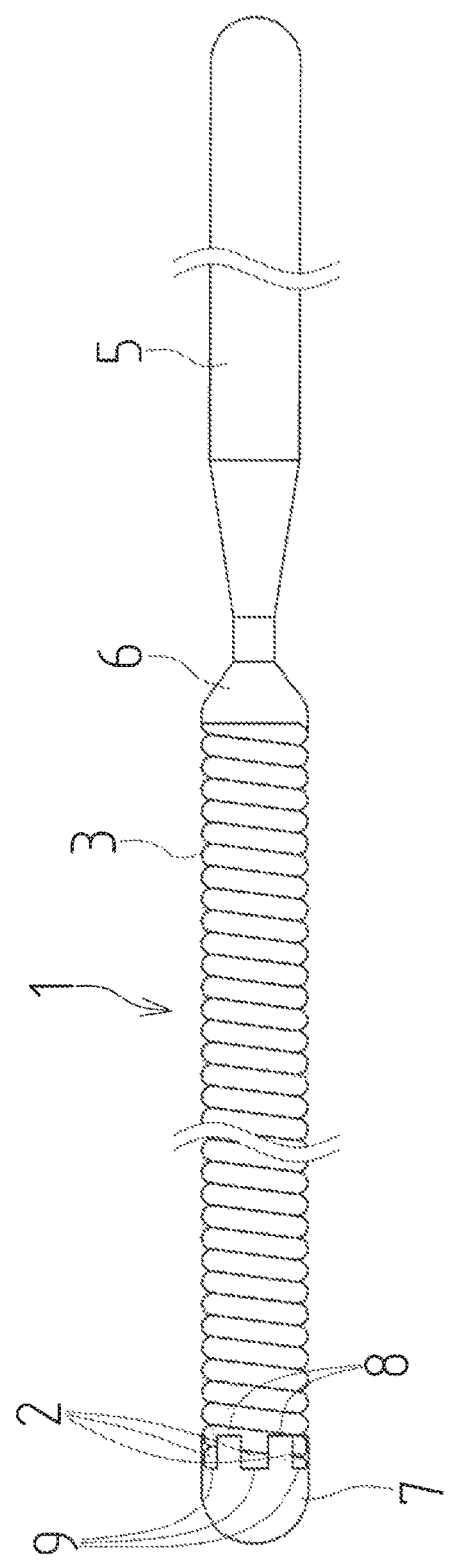
FIG. 1 shows an overall view of a guide wire according to the disclosed embodiments.
Figure 2:
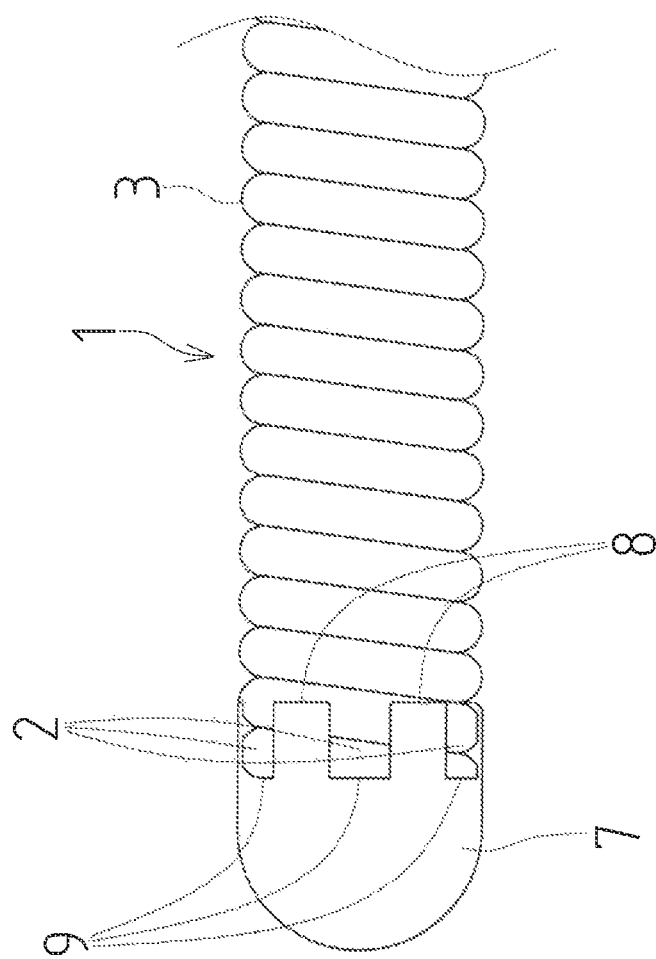
FIG. 2 shows an enlarged view of a distal end of the guide wire shown in FIG. 1.
Figure 3:
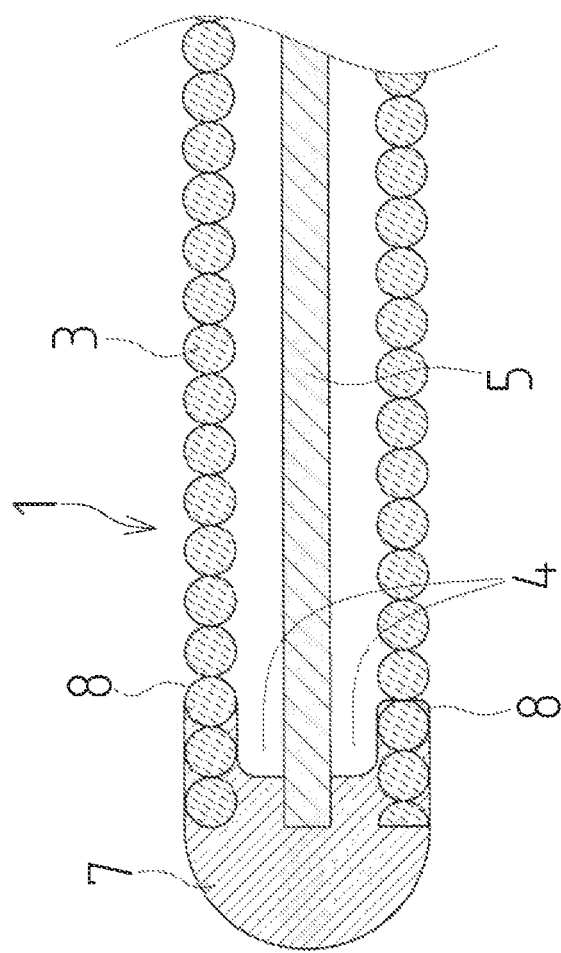
FIG. 3 shows a longitudinal cross-sectional view of the distal end of the guide wire shown in FIG. 2.

FIG. 1 shows an overall view of a guide wire according to the disclosed embodiments. FIG. 2 shows an enlarged view of a distal end of the guide wire shown in FIG. 1. FIG. 3 shows a longitudinal cross-sectional view of the distal end of the guide wire shown in FIG. 2. Throughout this disclosure, descriptions will be omitted for the parts already described, to which the same reference numbers will be assigned in the figures.

With reference to FIG. 1, a guide wire 1 comprises a core shaft 5, a coil body 3 covering (disposed around) a distal end part of the core shaft 5, a distal end joining portion 7 joining a distal end of the coil body 3 to a distal end of the core shaft 5, and a proximal end joining portion 6 joining a proximal end of the coil body 3 to the core shaft 5.

The core shaft 5 is a rod having a round cross section. The core shaft 5 is tapered from its proximal end toward its distal end. There is no particular limitation for the material of the core shaft 5, but stainless steel is used for purposes of this discussion. Superelastic alloys such as Ni—Ti alloy may also be used.

The coil body 3, which has a hollow cylindrical shape, is spirally wound around the core shaft 5. There is also no particular limitation for the material of the coil body 3, but stainless steel is used for purposes of this discussion. Tungsten may also be used.

Note that the coil body 3 is formed by winding one metal element wire at a relatively large twist angle with respect to the longitudinal direction of the guide wire 1.

The distal end joining portion 7, which has an approximately hemispherical shape, constitutes the distal end of the guide wire 1, and an outer diameter of a proximal end of the distal end joining portion 7 is approximately the same as an outer diameter of the coil body 3. There is no particular limitation for the material of the distal end joining portion 7, but an Ag—Sn-based solder material is used for purposes of this discussion. An Au—Sn-based solder material may also be used.

Further, the distal end joining portion 7 has a rectangular protruded portion 8 that protrudes proximally in the longitudinal direction of the guide wire 1, and a rectangular recessed portion 9 that extends distally in the longitudinal direction. That is, as seen in a cross section (which corresponds to the "cross-sectional view" described herein) of the distal end joining portion 7 cut in a direction perpendicular to the plane of the sheet of FIG. 2 (cut in a direction perpendicular to the longitudinal direction of the guide wire 1), the length of the distal end joining portion 7 in the longitudinal direction differs along an outer periphery of the distal end joining portion 7, and the rectangular protruded portion 8 and the rectangular recessed portion 9 form an uneven shape in the longitudinal direction.

An outer diameter of the proximal end joining portion 6 is approximately the same as the outer diameter of the coil body 3. There is no particular limitation for the material of the proximal end joining portion 6, but an Ag—Sn-based solder material is used for purposes of this discussion. An Au—Sn-based solder material may also be used.

In the guide wire 1, the proximal end of the distal end joining portion 7 is formed into an uneven shape in the longitudinal direction along the outer periphery of the distal end joining portion 7, and thus a distortion of the coil body 3 upon bending the guide wire 1 can be reduced by means of a space 2 defined by the rectangular protruded portion 8 and the rectangular recessed portion 9. As a result, the joining strength between the distal end joining portion 7 and the coil body 3 of the guide wire 1 can be improved, preventing the distal end joining portion 7 from detaching from the coil body 3.

Note that in FIG. 2, the rectangular protruded portion 8 does not extend along a length of the element wire of the coil body 3. However, the length of the protruded portion 8 can be altered so that the protruded portion 8 extends along a length of the element wire of the coil body 3 in order to further improve the joining strength between the distal end joining portion 7 and the coil body 3.

Further, distortion of the coil body 3 upon bending the guide wire 1 can also be reduced by means of a space 4 (gap) defined by the rectangular protruded portion 8 and the core shaft 5 as shown in FIG. 3. As a result, the joining strength between the distal end joining portion 7 and the coil body 3 can be improved, preventing the distal end joining portion 7 from detaching from the coil body 3.

Figure 4:
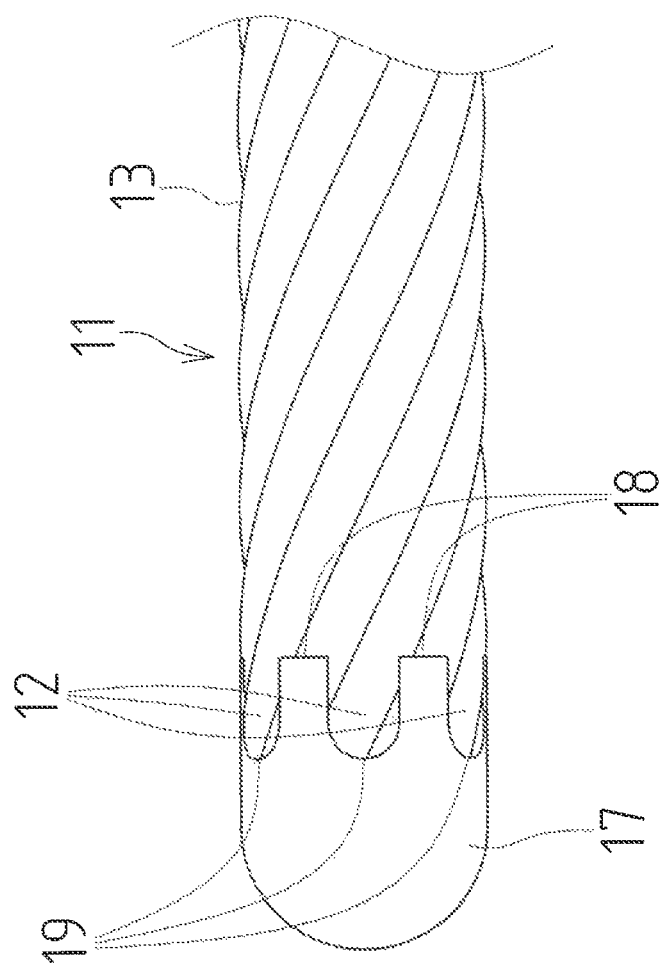
FIG. 4 shows an enlarged view of a distal end of a guide wire according to the disclosed embodiments.
Figure 5:
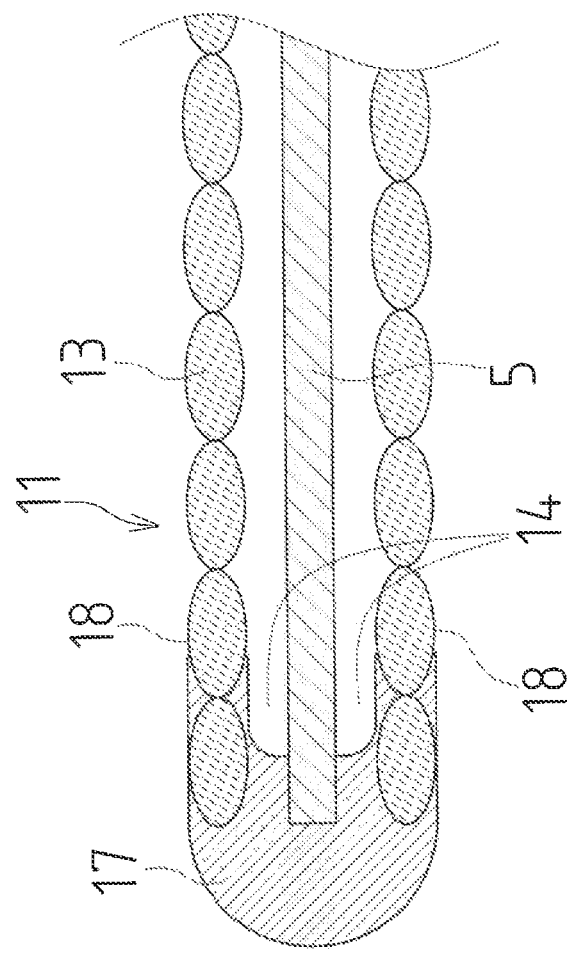
FIG. 5 shows a longitudinal cross-sectional view of the distal end of the guide wire shown in FIG. 4.

With reference to FIG. 4, a guide wire 11 comprises the core shaft 5, a coil body 13 covering the distal end part of the core shaft 5, and a distal end joining portion 17 joining a distal end of the coil body 13 to the distal end of the core shaft 5. FIG. 5 shows a longitudinal cross-sectional view of a distal end of the guide wire 11.

The coil body 13, which has a hollow cylindrical shape, is spirally wound around the core shaft 5. There is no particular limitation for the material of the coil body 13, but stainless steel is used for purposes of this discussion. Tungsten may also be used.

Note that the coil body 13 is formed by twisting multiple metal element wires (10 metal element wires as shown in FIG. 5) into a hollow cylindrical shape such that the twist angle with respect to the longitudinal direction of the guide wire 11 is relatively small.

The distal end joining portion 17, which has an approximately hemispherical shape, constitutes the distal end of the guide wire 11. There is no particular limitation for the material of the distal end joining portion 17, but an Au—Sn-based solder material is used for purposes of this discussion. An Au—Sn-based solder material may also be used.

Further, the distal end joining portion 17 has a rectangular protruded portion 18 that protrudes proximally in the longitudinal direction of the guide wire 11, and a curved recessed portion 19 that extends distally in the longitudinal direction. That is, as seen in the "cross-sectional view," the length of the distal end joining portion 17 in the longitudinal direction differs along an outer periphery of the distal end joining portion 17, and the rectangular protruded portion 18 and the curved recessed portion 19 form an uneven shape in the longitudinal direction.

In the guide wire 11, a proximal end of the distal end joining portion 17 is formed into an uneven shape in the longitudinal direction along the outer periphery of the distal end joining portion 17, and thus a distortion of the coil body 13 upon bending the guide wire 11 can be reduced by means of a space 12 defined by the rectangular protruded portion 18 and the curved recessed portion 19. In addition, stress is prevented from concentrating at the distal end joining portion 17 when the guide wire 11 is bent, further preventing detachment of the distal end joining portion 17 from the coil body 13.

Further, distortion of the coil body 13 upon bending the guide wire 11 can also be reduced by means of a space 14 (gap) defined by the rectangular protruded portion 18 and the core shaft 5. As a result, the joining strength between the distal end joining portion 17 and the coil body 13 can be improved, preventing the distal end joining portion 17 from detaching from the coil body 13.

Figure 6:
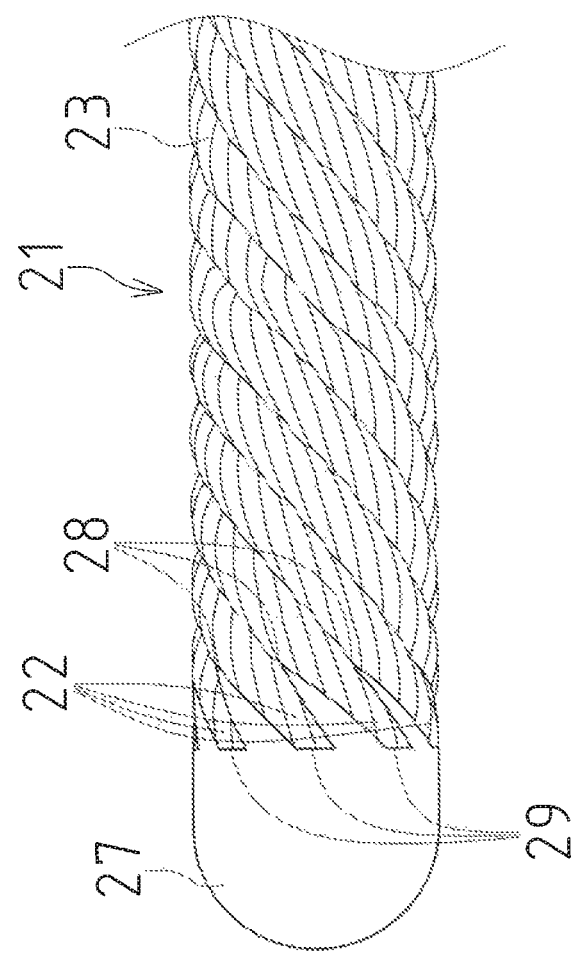
FIG. 6 shows an enlarged view of a distal end of a guide wire according to the disclosed embodiments.
Figure 7:
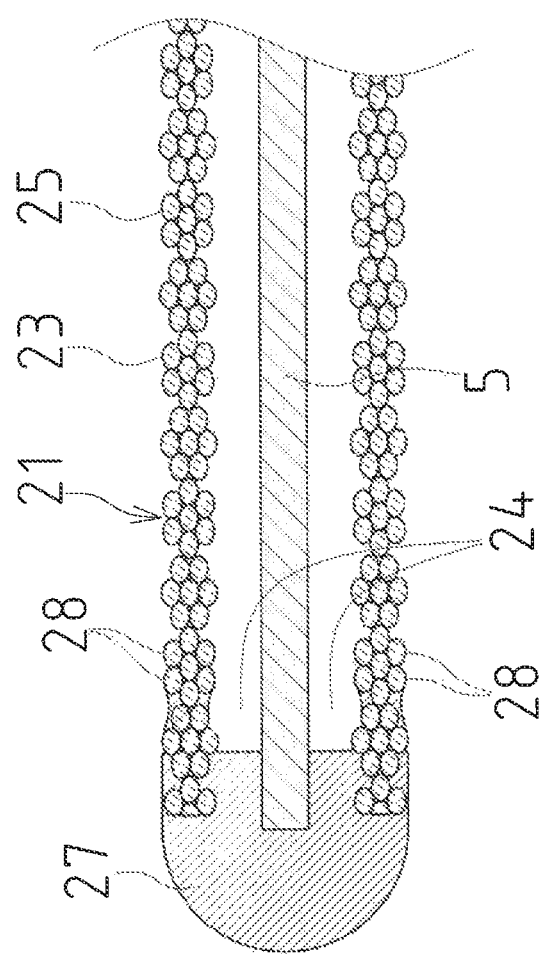
FIG. 7 shows a longitudinal cross-sectional view of the distal end of the guide wire shown in FIG. 6.

With reference to FIG. 6, a guide wire 21 comprises the core shaft 5, a coil body 23 covering the distal end part of the core shaft 5, and a distal end joining portion 27 joining a distal end of the coil body 23 to the distal end of the core shaft 5. FIG. 7 shows a longitudinal cross-sectional view of a distal end of the guide wire 21.

The coil body 23, which has a hollow cylindrical shape, is spirally wound around the core shaft 5. There is no particular limitation for the material of the coil body 23, but stainless steel is used for purposes of this discussion. Tungsten may also be used.

Note that the coil body 23 is formed by spirally winding 10 twisted wires 25 around the core shaft 5, the twisted wires 25 each being formed by twisting together 7 metal element wires (see FIG. 7).

The distal end joining portion 27, which has an approximately hemispherical shape, constitutes the distal end of the guide wire 21. There is no particular limitation for the material of the distal end joining portion 27, but an Ag—Sn-based solder material is used for purposes of this discussion. An Au—Sn-based solder material may also be used.

Further, the distal end joining portion 27 has a wedge-shaped protruded portion 28 that protrudes proximally in the longitudinal direction of the guide wire 21, and a rectangular recessed portion 29 that extends distally in the longitudinal direction. That is, as seen in the "cross-sectional view," the length of the distal end joining portion 27 in the longitudinal direction differs along an outer periphery of the distal end joining portion 27, and the wedge-shaped protruded portion 28 and the rectangular recessed portion 29 form an uneven shape in the longitudinal direction.

In the guide wire 21, a proximal end of the distal end joining portion 27 is formed into an uneven shape in the longitudinal direction along the outer periphery of the distal end joining portion 27, and thus a distortion of the coil body 23 upon bending the guide wire 21 can be reduced by means of a space 22 defined by the wedge-shaped protruded portion 28 and the rectangular recessed portion 29. In addition, a solder material constituting the distal end joining portion 27 is allowed to permeate between the metal element wires of the twisted wires 25 to improve the joining strength between the distal end joining portion 27 and the coil body 23 of the guide wire 21. This can further prevent detachment of the distal end joining portion 27 from the coil body 23.

Further, distortion of the coil body 23 upon bending the guide wire 21 can also be reduced by means of a space 24 (gap) defined by the wedge-shaped protruded portion 28 and the core shaft 5 as shown in FIG. 7. As a result, the joining strength between the distal end joining portion 27 and the coil body 23 can be improved, preventing the distal end joining portion 27 from detaching from the coil body 23.

Figure 8:
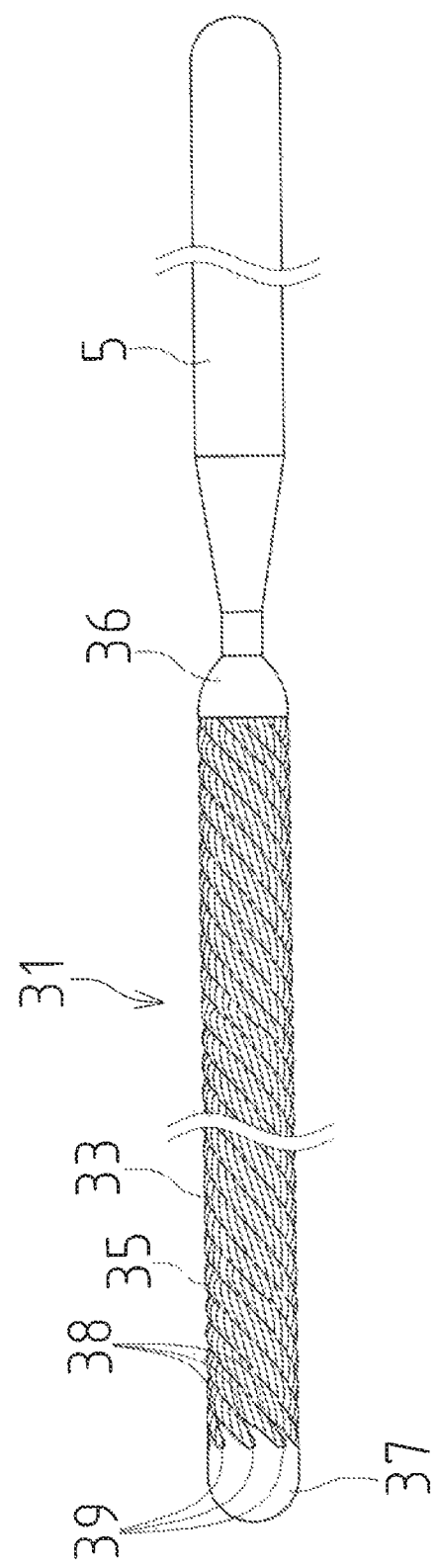
FIG. 8 shows an overall view of a guide wire according to the disclosed embodiments.
Figure 9:
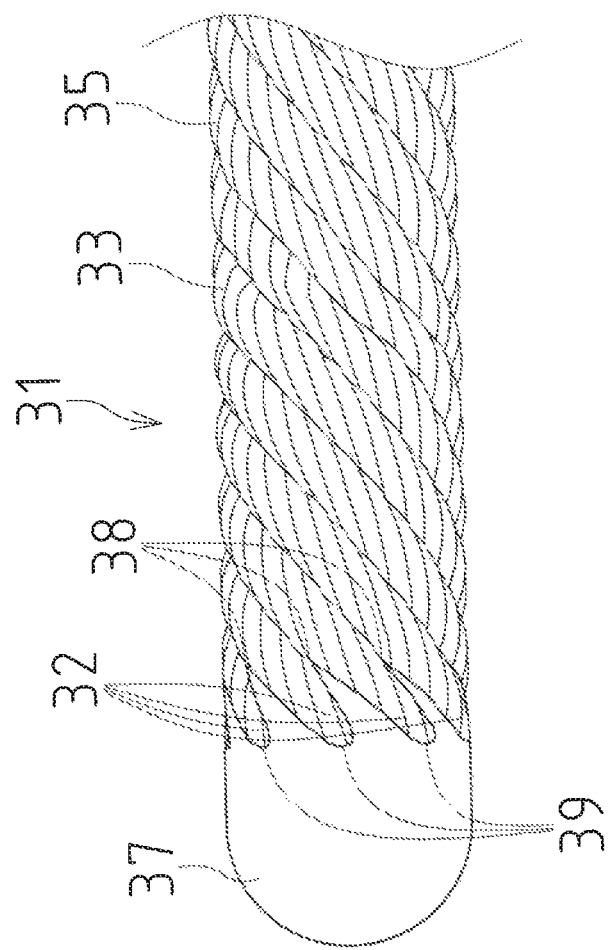
FIG. 9 shows an enlarged view of a distal end of the guide wire shown in FIG. 8.

With reference to FIG. 8, a guide wire 31 comprises the core shaft 5, a coil body 33 covering the distal end part of the core shaft 5, a distal end joining portion 37 joining a distal end of the coil body 33 to the distal end of the core shaft 5, and a proximal end joining portion 36 joining a proximal end of the coil body 33 to the core shaft 5. FIG. 9 shows an enlarged view of a distal end of the guide wire 31. Note that a longitudinal cross-sectional view is omitted because it is the same as FIG. 7.

The coil body 33, which has a hollow cylindrical shape, is spirally wound around the core shaft 5. There is no particular limitation for the material of the coil body 33, but stainless steel is used for purposes of this discussion. Tungsten may also be used.

Note that the coil body 33 is formed by spirally winding 10 twisted wires 35 around the core shaft 5, the twisted wires 35 each being formed by twisting 7 Metal element wires as in the coil body 23.

The distal end joining portion 37, which is of an approximately hemispherical shape, constitutes the distal end of the guide wire 31. There is no particular limitation for the material of the distal end joining portion 37, but an Ag—Sn-based solder material is used for purposes of this discussion. An Au—Sn-based solder material may also be used.

Further, the distal end joining portion 37 has a wedge-like protruded portion 38 that protrudes proximally in the longitudinal direction of the guide wire 31, and a curved recessed portion 39 that extends distally in the longitudinal direction. That is, as seen in the "cross-sectional view," the length of the distal end joining portion 37 in the longitudinal direction differs along an outer periphery of the distal end joining portion 37, and the wedge-shaped protruded portion 38 and the curved recessed portion 39 form an uneven shape in the longitudinal direction.

An outer diameter of the proximal end joining portion 36 at the distal end part is approximately the same as an outer diameter of the coil body 33. There is no particular limitation for the material of the distal end joining portion 36, but an Ag—Sn-based solder material is used for purposes of this discussion. An Au—Sn-based solder material may also be used.

In the guide wire 31, a proximal end of the distal end joining portion 37 is formed into an uneven shape in the longitudinal direction along the outer periphery of the distal end joining portion 37, and thus a distortion of the coil body 33 upon bending the guide wire 31 can be reduced by means of a space 32 defined by the wedge-shaped protruded portion 38 and the curved recessed portion 39.

Further, a solder material constituting the distal end joining portion 37 is allowed to permeate between the metal element wires of the twisted wires 35 to further improve the joining strength between the distal end joining portion 37 and the coil body 33 of the guide wire 31. Stress is prevented from concentrating at the distal end joining portion 37 when the guide wire 11 is bent, which in turn prevents the distal end joining portion 37 from detaching from the coil body 33.

The present invention shall not be limited to the embodiments described above. The present invention may be practiced with various modifications made without departing from the scope of the present invention.

For example, the coil bodies of the guide wires according to the above embodiments are formed with metal element wires, but they may be formed with one or more resin element wires. However, a coil body formed with one or more metal element wires may be convenient when the distal end joining portion comprises a solder material.

Further, the distal end joining portions in the aforementioned embodiments are made of an Ag—Sn-based solder material or an Au—Sn-based solder material, but a core shaft may be also fixed to a coil body with an adhesive. However, an Ag—Sn-based solder material or an Au—Sn-based solder material can provide a better bonding strength based on previous experiences.

What is claimed is:

1. A guide wire comprising:
a core shaft;
a coil body disposed around an outer periphery of the core shaft; and
a joining portion joining a distal end of the core shaft to a distal end of the coil body,
wherein:
a proximal end of an outer periphery of the joining portion comprises a plurality of protruded portions that protrude proximally in a longitudinal direction of the guide wire,
spaces between the protruded portions define recessed portions, and
a length of the joining portion in the longitudinal direction from a distal end of the joining portion to a proximal end of the joining portion differs along an outer circumference of the joining portion.

2. The guide wire according to claim 1, wherein at least one of the protruded portions has a rectangular shape.

3. The guide wire according to claim 1, wherein at least one of the protruded portions has a wedge shape.

4. The guide wire according to claim 1, wherein the guide wire includes a space between the protruded portions and the core shaft.

5. The guide wire according to claim 1, wherein the coil body comprises multiple element wires.

6. The guide wire according to claim 1, wherein the coil body comprises multiple twisted wires, each having multiple element wires twisted together.

7. The guide wire according to claim 6, wherein a solder material constituting the joining portion permeates between the metal element wires of the twisted wires.

8. The guide wire according to claim 2, wherein the coil body comprises multiple twisted wires, each having multiple element wires twisted together.

9. The guide wire according to claim 3, wherein the coil body comprises multiple twisted wires, each having multiple element wires twisted together.

10. The guide wire according to claim 1, wherein each of the recessed portions has a rectangular shape.

11. The guide wire according to claim 1, wherein each of the recessed portions has a curved shape.

* * * * *